US00PP27626P2

(12) United States Plant Patent
Zaiger et al.

(10) Patent No.: US PP27,626 P2
(45) Date of Patent: Jan. 31, 2017

(54) NECTARINE TREE NAMED 'POLAR MAGIC'

(50) Latin Name: ***Prunus persica* var. *nucipersica***
Varietal Denomination: Polar Magic

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 17 days.

(21) Appl. No.: 14/756,155

(22) Filed: Aug. 10, 2015

(51) Int. Cl.
*A01H 5/08* (2006.01)

(52) U.S. Cl.
USPC ..... Plt./188

(58) Field of Classification Search
USPC ..... Plt./188
See application file for complete search history.

*Primary Examiner* — June Hwu

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, upright growth habit.
2. Regular and productive bearer of large size fruit.
3. Fruit having very good flavor and eating quality with a good balance between acid and sugar.
4. Fruit with attractive red skin color.
5. Clingstone fruit with firm, white flesh.

1 Drawing Sheet

Botanical designation: *Prunus persica* var. *nucipersica*.
Variety denomination: 'Polar Magic'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

Prior Varieties

Among the existing varieties of nectarine trees, which are known to us, and mentioned herein, 'Honey Royale' Nectarine (U.S. Plant Pat. No. 12,008), 'Honey Kist' Nectarine (U.S. Plant Pat. No. 9,333), 'Honey Haven' Nectarine (U.S. Plant Pat. No. 12,393) and our proprietary non-patented nectarine seedlings '184LT187', '56Z762' and '219LK242'.

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was developed by us in our experimental orchard located near Modeto, Calif. as a first generation cross between our proprietary non-patented nectarine seedlings '184LT187' and '219LK242'. The seed parent (184LT187) originated from the cross of our non-patented nectarine seedling selection '56Z762' and 'Honey Royale' Nectarine (U.S. Plant Pat. No. 12,008). The pollen parent (219LK242) originated as an open pollinated seedling selection from seed of 'Honey Kist' Nectarine (U.S. Plant Pat. No. 9,333). A large number of these first generation seedlings were budded onto older established trees of 'Nemaguard' Rootstock (non-patented) to enhance earlier fruit production. Under close and careful observation the present budded seedling exhibited desirable fruit and tree characteristics and was selected in 2007 for additional asexual propagation and commercialization.

ASEXUAL REPRODUCTION OF THE VARIETY

In 2007 asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of nectarine tree (*Prunus persica* var. *nucipersica*) is of large size, vigorous, upright growth and a regular and productive bearer of large size, white flesh fruit with attractive red skin color. The fruit is further characterized by having very good flavor and eating quality and good handling and storage quality. In comparison to its proprietary non-patented nectarine seed parent (184LT187)

the fruit of the new variety is larger in size, better coverage of attractive red skin color and the tree sets a consistently heavy crop. In comparison to its pollen parent (219LK242) the fruit of the new variety has improved flavor and is approximately 25 days earlier in maturity. In comparison to the commercial variety 'Honey Haven' Nectarine (U.S. Plant Pat. No. 12,393) the fruit of the new variety has white flesh compared to yellow and is approximately 7 days earlier in maturity.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 7 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height and width the first growing season. Varies slightly with type and fertility of soil, climatic conditions and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 5 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 650 hours at or below 45° F.

Trunk:

*Size*.—Large, average circumference 55.9 cm at 25.4 cm above ground on a 7 year old tree.

*Stocky*.—Medium stocky.

*Texture*.—Medium shaggy, roughness increases with age.

*Color*.—Varies from 2.5Y 3/2 to 2.5Y 2/2.

Branches:

*Size*.—Medium. Average circumference 19.3 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 18 in a 25.8 square cm area. Average length 4.2 mm. Average width 2.4 mm. Color varies from 2.5Y 5/8 to 2.5Y 4/6.

*Color*.—New growth varies from 5GY 7/6 to 5GY 6/6. Mature growth varies from 2.5Y 4/4 to 2.5Y 5/6, varies with age of growth.

Leaves:

*Size*.—Medium. Average length 145.9 mm. Average width 43.2 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 8.3 mm. Average width 1.7 mm. Longitudinally grooved. Surface — glabrous. Color varies from 5GY 7/4 to 5GY 7/6.

*Glands*.—Type — reniform. Size — large. Average length 1.6 mm. Average diameter 1.0 mm. Number varies from 3 to 5, average number 4. Located primarily on the base of the leaf blade and upper portion of petiole. Color varies from 5GY 7/8 to 5GY 6/8.

*Stipules*.—Average number 2. Average length 7.8 mm. Edges pectinate. Color varies from 5GY 7/6 to 5GY 7/8.

*Color*.—Upper surface varies from 5GY 4/6 to 5GY 3/6. Lower surface varies from 5GY 5/4 to 5GY 4/4. Midvein color varies from 5GY 7/4 to 5GY 7/6.

Flower buds:

*Size*.—Large. Average length 20.8 mm. Average diameter 11.4 mm.

*Hardiness*.—Hardy with respect to California winters.

*Density*.—Dense.

*Form*.—Conical, becoming elongated just before opening.

*Pedicel*.—Average length 4.2 mm. Average width 1.1 mm. Surface — glabrous. Color varies from 5GY 8/8 to 5GY 7/8.

*Color*.—Varies from 5RP 9/2 to 5RP 8/6.

Flowers:

*Blooming period*.—Date of First Bloom Feb. 16, 2015. Date of Petal Fall Feb. 26, 2015, varies slightly with climatic conditions.

*Size*.—Large, showy. Average height 21.1 mm. Average diameter 51.8 mm.

*Petals*.—Normally 5, alternately arranged to sepals. Size — large. Average length 24.1 mm. Average width 21.2 mm. Form — orbicular. Petal apex — rounded. Petal base truncate. Margin — sinuate. Arrangement— overlapping. Both upper and lower surfaces glabrous. Color varies from 2.5RP 9/2 to 2.5RP 6/10, fades with age of flowers.

*Sepals*.—Normally 5, alternately arranged to petals. Size — large. Average length 7.4 mm. Average width 6.8 mm. Shape — ovate, apex rounded to triangular. Margin — entire. Color — upper surface varies from 5GY 4/8 to 7.5GY 5/8. Lower surface varies from 10RP 3/10 to 10RP 2/8. Surface — upper surface glabrous, lower surface pubescent.

*Stamens*.—Average number per flower 49. On average, the stamens are equal to the height of the petals. Filament color varies from N 9.5/(white) to 5RP 7/6, depending on age of flower. Anther color varies from 7.5R 4/12 to 5Y 8/8.

*Pollen*.—Self fertile. Color 5Y 7/12.

*Pistil*.—Normally one. Average length 21.4 mm. Position of stigma an average of 1.2 mm above anthers. Surface — glabrous. Color varies from 10Y 8/6 to 2.5GY 8/6.

*Fragrance*.—Moderate.

*Color*.—Varies from 5RP 8/4 to 5RP 6/10.

*Pedicel*.—Average length 5.9 mm. Average width 1.5 mm. Color varies from 5GY 8/8 to 5GY 7/12. Surface — glabrous.

*Number flowers per flower bud*.—Normally one.

Fruit:

*Maturity when described*.—Firm ripe and ready for consumption.

*Date of first picking*.—Jun. 8, 2015.

*Date of last picking*.—Jun. 18, 2015, varies slightly with climatic conditions.

*Size*.—Large. Average diameter axially 69.6 mm. Average transversely in suture plane 71.0 mm. Average weight 207.3 grams, varies slightly with fertility of soil, amount of thinning and climatic conditions.

*Form*.—Globose to slightly elongated.

*Suture*.—Slightly lipped.

*Ventral surface*.—Slightly lipped.

*Apex*.—Slightly retuse.

*Base*.—Retuse.

*Stem cavity*.—Rounded to slightly elongated in suture plane. Average depth 8.9 mm. Average diameter 8.3 mm.

Stem:

*Size*.—Small. Average length 9.7 mm. Average diameter 3.4 mm.

*Color*.—Varies from 5GY 6/6 to 5GY 5/8.

Flesh:

*Ripens*.—Evenly.

*Texture*.—Firm, meaty, crisp.

*Fibers*.—Few, small, tender.

*Firmness*.—Firm, comparable to other commercial varieties.

*Aroma*.—Slight.

*Amydgalin*.—Undetected.

*Eating quality*.—Very good.

*Flavor*.—Very good, good balance between acid and sugar.

*Juice*.—Moderate amount, enhances flavor.

*Acidity*.—Not available.

*Brix*.—Average Brix 14.0°, varies slightly with amount of fruit per tree and climatic conditions.

*Pit cavity*.—Average length 42.5 mm. Average width 24.4 mm. Average depth 11.2 mm. Color varies from 7.5Y 8.5/4 to 7.5Y 8/4.

*Color*.—Varies from 7.5Y 8.5/4 to 10Y 9/2.

Skin:

*Thickness*.—Medium.

*Surface*.—Smooth.

*Pubescence*.—Wanting.

*Tendency to crack*.—None.

*Color*.—Ground color varies from 5Y 8.5/4 to 7.5Y 8.5/4. Overspread with 7.5R 3/10 to 7.5R 2/8.

*Tenacity*.—Tenacious to the flesh.

*Astringency*.—Undetected.

Stone:

*Type*.—Clingstone, strong adherence to flesh.

*Size*.—Large. Average length 41.5 mm. Average width 23..4 mm. Average thickness 20.3 mm.

*Form*.—Ovoid.

*Base*.—Flat.

*Apex*.—Pointed. Average length 3.3 mm.

*Surface*.—Pitted throughout, pits vary from rounded to elongated.

*Sides*.—Unequal, one side extending further from suture plane.

*Ridges*.—Relatively smooth, extending from base to apex.

*Tendency to split*.—Slight.

*Color*.—Varies from 5YR 5/8 to 7.5YR 5/8 when dry.

Kernel:

*Size*.—Large. Average length 20.9 mm. Average width 11.2 mm. Average depth 8.6 mm.

*Form*.—Ovoid.

*Viability*.—Partially viable, not all embryos fully developed.

*Skin color*.—Varies from 7.5Y 9/4 to 10Y 9/2.

Use:

*Dessert*.—Market — local and long distance.

Keeping quality: Good, held firm in cold storage 2 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

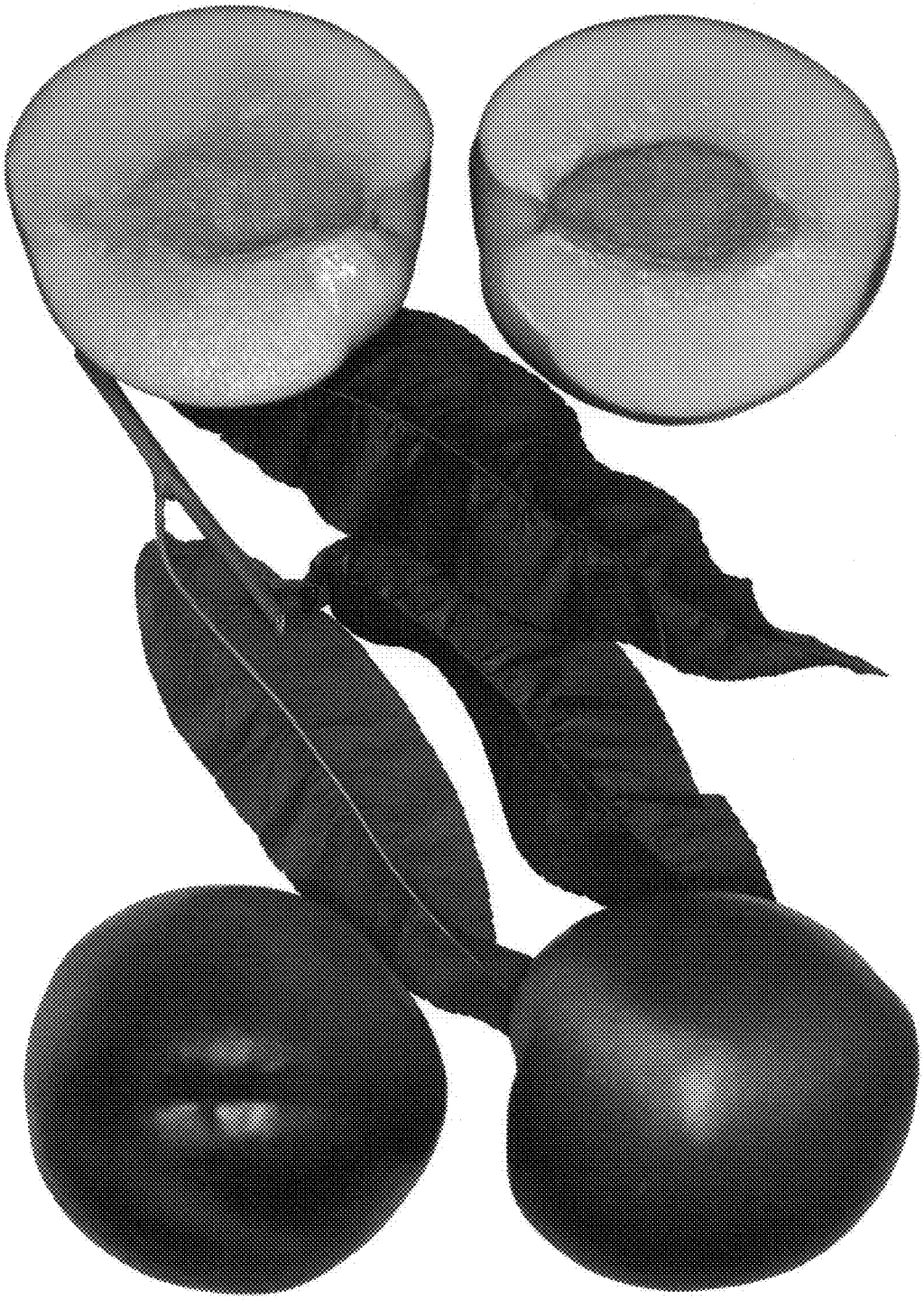

* * * * *